(12) United States Patent
Khirabadi et al.

(10) Patent No.: US 7,157,222 B2
(45) Date of Patent: *Jan. 2, 2007

(54) METHOD OF CRYOPRESERVATION OF TISSUES BY VITRIFICATION

(75) Inventors: Bijan S. Khirabadi, Rockville, MD (US); Ying C. Song, Mt. Pleasant, SC (US); Kelvin G. M. Brockbank, Charleston, SC (US)

(73) Assignee: Organ Recovery Systems, Inc., DesPlaines, IL (US)

( * ) Notice: Subject to any disclaimer, the term of this patent is extended or adjusted under 35 U.S.C. 154(b) by 413 days.

This patent is subject to a terminal disclaimer.

(21) Appl. No.: 10/646,802

(22) Filed: Aug. 25, 2003

(65) Prior Publication Data

US 2005/0100876 A1 May 12, 2005

Related U.S. Application Data

(60) Division of application No. 09/691,197, filed on Oct. 19, 2000, now Pat. No. 6,740,484, which is a continuation-in-part of application No. 09/289,977, filed on Apr. 13, 1999, now Pat. No. 6,194,137.

(51) Int. Cl.
*A01N 1/02* (2006.01)

(52) U.S. Cl. ...................................... 435/1.3
(58) Field of Classification Search ................ None
See application file for complete search history.

(56) References Cited

U.S. PATENT DOCUMENTS

| | | | |
|---|---|---|---|
| 4,494,385 A | 1/1985 | Kuraoka et al. | |
| 4,559,298 A | 12/1985 | Fahy | |
| 5,122,110 A | 6/1992 | McNally et al. | |
| 5,145,769 A | 9/1992 | McNally et al. | |
| 5,149,621 A | 9/1992 | McNally et al. | |
| 5,158,867 A | 10/1992 | McNally et al. | |
| 5,217,860 A | 6/1993 | Fahy et al. | |
| 5,472,876 A | 12/1995 | Fahy | |
| 5,518,878 A | 5/1996 | Wilkins et al. | |
| 5,723,282 A | 3/1998 | Fahy et al. | |
| 5,821,045 A | 10/1998 | Fahy et al. | |
| 5,856,081 A | 1/1999 | Fahy | |
| 5,873,254 A | 2/1999 | Arav | |
| 5,962,214 A | 10/1999 | Fahy et al. | |
| 6,194,137 B1 | 2/2001 | Khirabadi et al. | |

FOREIGN PATENT DOCUMENTS

| | | |
|---|---|---|
| WO | WO 96/05727 | 2/1996 |
| WO | WO 00/60935 | 10/2000 |
| WO | WO 01/78504 | 10/2001 |

OTHER PUBLICATIONS

Pegg et al., "Fractures in Cryopreserved Elastic Arteries", Cryobiology 34 : 183-192 (1997).*

Armitage, "Survival of Corneal Endothelium following Exposure to a Vitrification Solution," CRYOBIOLOGY, vol. 26, 1989, pp. 318-327.

Bourne et al., "Human Corneal Studies with a Vitrification Solution Containing Dimethyl Sulfoxide, Formamide, and 1,2-Propanediol," CRYOBIOLOGY, vol. 31, No. 6, 1994, pp. 522-530.

Dent et al., "Cryopreservation of Vein Grafts," Surgical Forum, vol. 25, pp. 241-243, 1974.

Brockbank et al., "Cryopreserved Vein Transplantation," Journal of Cardiac Surgery, vol. 7, No. 2, pp. 170-176, 1992.

Müller-Schweinitzer, "Cryopreservation: a useful technique for storing tissues for pharmacological investigations," Trends in Pharmacological Sciences; vol. 9, No. 6, pp. 221-223; Jun. 1988.

Weber et al., "Viable Vein Graft Preservation," Journal of Surgical Research 18, pp. 247-255, 1975.

Bishop et al., "A morphological assessment of vein allografts preserved in glycerol and used for arterial replacement," Journal of Cardiovascular Surgery 28, pp. 491-497, 1987.

Barner et al., "Fresh and Frozen Homologous Venous Grafts for Arterial Repair," Angiology 17, pp. 389-401, 1966.

Sitzmann et al., "Dimethylsulfoxide-treated, cryopreserved venous allografts in the arterial and venous systems," Surgery, vol. 95, No. 2, pp. 154-159, 1984.

Song et al., "Cryopreservation of the Common Carotid Artery of the Rabbit: Optimization of Dimethyl Sulfoxide Concentration and Cooling Rate," Cryobiology 32, pp. 405-421, 1995.

Wusterman et al., "The Effect of Cooling Rate and Temperature on the Toxicity of Ethylene Glycol in the Rabbit Internal Carotid Artery," Cryobiology 33, pp. 423-429, 1996.

Narayanan et al., "Successful Cryopreservation of Microvenous Allografts," Journal of Investigative Surgery, vol. 5, pp. 155-160, 1992.

(Continued)

*Primary Examiner*—Sandra E Saucier
(74) *Attorney, Agent, or Firm*—Oliff & Berridge, PLC

(57) ABSTRACT

A method for vitrification of a tissue or organ includes immersing the tissue or organ in increasing concentrations of cryoprotectant solution at a temperature greater than −15° C. to a cryoprotectant concentration sufficient for vitrification; cooling the tissue or organ at an average rate of from 2.5–100° C. per minute to a temperature between −80° C. and the glass transition temperature; and further cooling the tissue or organ at an average rate less than 30° C. per minute to a temperature below the glass transition temperature to vitrify the tissue or organ. After the vitrified tissue or organ has been stored, the tissue or organ may be removed from vitrification by warming the tissue or organ at an average rate of from 20–40° C. per minute to a temperature between −80° C. and the glass transition temperature; further warming the tissue or organ at a rate greater than 80° C. per minute to a temperature above −75° C.; and reducing the concentration of the cryoprotectant. Tissues or organs treated in this manner exhibit near normal functions, for example, blood vessels exhibit near normal smooth muscle contractility and normal graft functions.

25 Claims, 7 Drawing Sheets

OTHER PUBLICATIONS

Ku et al., "Human Coronary Vascular Smooth Muscle and Endothelium-Dependent Responses after Storage at -75° C," Cryobiology 29, pp. 199-209, 1992.

Müller-Schweinitzer et al., "Sucrose promotes the functional activity of blood vessels after cryopreservation in DMSO-containing fetal calf serum," Naunyn-Schmiedeberg's Archives of Pharmacology, pp. 1-4, 1992.

Müller-Schweinitzer et al., "Functional recovery of human mesenteric and coronary arteries after cryopreservation at—196° C in a serum-free medium," Journal of Vascular Surgery, vol. 25, No. 4, pp. 743-749, 1997.

Fahy et al., G. M., "Vitrification as an Approach to Cryopreservation," Cryobiology 21, pp. 407-426, 1984.

Chen et al., X. H., "Vitrification of Multicomponent Solutions by Cooling to Cryogenic Temperatures," Cryogenics vol. 30 Sept. Supplement, pp. 541-545, 1990.

Fahy et al., G. M., "Some Emerging Principles Underlying the Physical Properties, Biological Actions, and Utility of Vitrification Solutions," Cryobiology 24, pp. 196-213, 1987.

Ren et al., H. S., "The Crystallization Kimetics and the Critical Cooling Rates for Vitrification of Cryoprotective Solutions," Cryogenics 1990, vol. 30, Sep. Supplement, pp. 536-540.

Guttman et al., Frank M., "Variation of Cooling Rate and Concentration of Dimethyl Sulfoxide on Rabbit Kidney Function," Cryobiology, 23, pp. 495-499, 1986.

Jacobsen et al., I.A., "Effect of Cooling and Warming Rate on Glycerolized Rabbit Kidneys," Cryobiology 19:668, 1982.

F. Binette et al., "Expression of a Stable Articular Cartilage Phenotype Without Evidence of Hypertrophy by Adult Human Articular Chondrocytes In Vitro", Journal of Orthopaedic Research, vol. 16, pp. 207-216, 1998.

Y. Song et al., "Vitreous Cryopreservation Maintains the Function of Vascular Grafts", Nature Biotechnology, vol. 18, pp. 296-299, 2000.

T. Fujita, MD, PhD, et al., "Successful Preservation of Human Skin by Vitrification", Journal of Burn Care & Rehabilitation, vol. 21, No. 4, pp. 304-309, 2000.

B. Stone et al., "Cryopreservation of Human Articular Cartilage for Autologous Chondrocyte Implantation", Cryobiology, (Abstracts, 35th Annual Meeting), vol. 37, No. 4, pp. 445-446, 1998.

Abstracts, 36th Annual Meeting of the Society for Cryobiology, "Vitrification of the Rabbit Cornea", Cryobiology, vol. 38, pp. 310, 1999.

D.E. Pegg et al., "Fractures in Cryopreserved Elastic Arteries," Abstract Only, Database Accession No. PREV199799558143, Cryobiology, vol. 34, No. 2, pp. 183-192, 1997.

\* cited by examiner

Fresh 2 Week Grafts — Vitrified 4 Week Grafts

A    Graft at implantation    B

C    Graft after perfusion fixation and removal    D

E    Graft dissection    F

METHOD OF CRYOPRESERVATION OF TISSUES BY VITRIFICATION

This application is a division of U.S. patent application Ser. No.09/691,197, filed Oct. 19, 2000 now U.S. Pat. No. 6,740,484, which in turn is a continuation-in-part of U.S. patent application Ser. No. 09/289,977, filed Apr. 13, 1999, now U.S. Pat. No. 6,194,137. The entire contents of these prior applications are hereby incorporated by reference.

The U.S. Government has a paid-up license in this invention and the right in limited circumstances to require the patent owner to license others on reasonable terms as provided by the terms of cooperative agreement No. 70NANB7H3071 awarded by NIST.

BACKGROUND OF THE INVENTION

The supply of viable tissues and cells for autologous implantation and heterologous transplantation (hereinafter jointly referred to as transplantation) and study is limited in part by the time a tissue or organ can be maintained in a viable state. Increasing the length of time that a tissue or organ remains viable may drastically increase the likelihood that a particular tissue or organ reaches a recipient or researcher in a viable state.

The transplantation of tissues, natural or engineered, including vascularized tissues and avascular tissues, including, but not limited to, vascular tissue, such as blood vessels, musculoskeletal tissue, such as cartilage, menisci, muscles, ligaments and tendons, skin, cardiovascular tissue, such as heart valves and myocardium, neuronal tissue, periodontal tissue, glandular tissue, organ tissue, islets of Langerhans, cornea, ureter, urethra, breast tissue, and organs, intact or sections thereof, such as pancreas, bladder, kidney, liver, intestine and heart, may all be benefited by increasing the length of time that such tissues and organs remain viable. In the present era of arterial replacement, at least 345,000–485,000 autologous coronary grafts (either arteries or veins) and over 200,000 autogenous vein grafts into peripheral arteries are performed each year. Report of a working party of the British Cardiac Society: Coronary Angioplasty in the United Kingdom. *Br Heart J.* 66:325–331, 1991; Heart and Stroke Facts: Statistical Supplement, American Heart Association, 1996; and Callow AD. "Historical overview of experimental and clinical development of vascular grafts," In: Biologic and Synthetic Vascular Prosthesis, Stanley J (Ed), Grune and Stratton, New York, 11, 1983. A recent marketing report indicated that at least 300,000 coronary artery bypass procedures are performed annually in the United States involving in excess of 1 million vascular grafts. World Cell Therapy Markets, Frost & Sullivan, 5413–43 Revision #1, ISBN 0-7889-0693-3, 1997.

Many of these patients do not have autologous veins suitable for grafts due to pre-existing vascular disease, vein stripping or use in prior vascular procedures. It has been estimated that as many as 30% of the patients who require arterial bypass procedures will have saphenous veins unsuitable for use in vascular reconstruction. Edwards W S, Holdefer W F, Motashemi, M, "The importance of proper caliber of lumen in femoral popliteal artery reconstruction," *Surg Gynecol Obstet.* 122:37, 1966. More recently it has been demonstrated that 2–5% of saphenous veins considered for bypass procedures were unusable on the basis of gross pathology and that up to 12% were subsequently classified as diseased. These "diseased" veins had patency rates less than half that of non-diseased veins. Panetta T F, Marin M L, Veith F J, et al., "Unsuspected pre-existing saphenous vein disease: an unrecognized cause of vein bypass failure," *J Vasc Surg.* 15:102–112, 1992. However, we estimate that if all arterial grafts and alternative veins are utilized according to current surgical practice, the maximum number of potential allograft recipients is probably closer to 10%.

Vitrified arterial grafts may also have a market as a scaffold for the seeding and adhesion of autologous endothelial cells or genetically modified endothelial cells. Prosthetic grafts are currently employed for large diameter (greater than 6 mm internal diameter) non-coronary applications. Between 1985 and 1990, approximately 1,200 allogeneic vein segments were employed for arterial bypass. Brockbank K G M, McNally R T, Walsh K A, "Cryopreserved vein transplantation," *J Cardiac Surg.* 7:170–176, 1992. The demand for allogeneic veins is growing despite the well documented immune response to these grafts and the low clinical patency rates. In 1991 alone, at least 1,400 allograft saphenous vein segments were transplanted. McNally R T, Walsh K, Richardson W, "Early clinical evaluation of cryopreserved allograft vein," Proceedings of the 29$^{th}$ meeting of the Society for Cryobiology, *Cryobio.*, Abstract #4, 1992. Conservatively, the market potential for vitrified vascular grafts may be 50,000 units per year, or 10% of all vascular grafting procedures in the United States.

Blood vessels are also a ubiquitous component of vascularized tissues and organs, both human and animal, which may one day be successfully stored by vitrification for transplantation. Providing that significant immunological issues can be overcome, animal-derived grafts may, one day, provide an unlimited supply of blood vessels and vascularized tissues and organs that could be stored in a vitrified state prior to transplantation.

Avascular tissues may also be used for transplantation. For example, on average, an orthopedic surgeon specializing in knee surgery will treat between 10–20 patients per year who have sustained traumatic, full-thickness articular cartilage injuries. These patients may all be candidates for cartilage implantation. Approximately 30% of all Anterior Cruciate Ligament (ACL) tears have an associated full-thickness cartilage defect that often is undetected, even after surgery. For example, it was estimated that 20.4% of the 392,568 patients who received cartilage repairs in 1996 were candidates for a cartilage implant.

Over time, most full-thickness defects deteriorate and cause significant joint impairment. Since cartilage is avascular, the recruitment of cells to aid healing of partial thickness defects is difficult. In contrast, full-thickness defects have the potential for partial healing when techniques such as abrasion arthroplasty are employed. Unfortunately, however, these procedures generally result in mechanically inferior fibrous scars.

Fresh osteochondral allografts have proven to be effective and functional for transplantation. The limited availability of fresh allograft tissues, however, necessitates the use of osteoarticular allograft banking for long-term storage. Although cryopreservation involving freezing is a preferred method for storing tissue until needed, conventional protocols result in death of 80–100% of the chondrocytes and damage to the extracellular matrix due to ice formation. These detrimental effects are the main obstacles preventing successful clinical outcome. Various studies using animal articular cartilage models and human cartilage biopsies have revealed no more than 20% chondrocyte viability following conventional cryopreservation procedures employing either dimethyl sulfoxide (DMSO) or glycerol as cryoprotectants. Such results greatly limit the possibilities for transplantation or grafting harvested cartilage.

Low temperature preservation of biological tissues and organs, i.e., cryopreservation, has been the subject of much research effort. Cryopreservation can be approached by freezing or by vitrification. If the organ or tissue is frozen, ice crystals may form within the organ or tissue that may mechanically disrupt its structure and thus damage its ability to function correctly when it is transplanted into a recipient. Organized tissues and organs are particularly susceptible to mechanical damage from ice crystals formed during freezing.

Even when all cryopreservation variables are controlled, there is a limit, which is largely a function of tissue volume and geometry (including any associated fluids and packaging), beyond which traditional cryopreservation methods do not consistently work. For example, in cryopreserved allograft heart valves, the leaflet fibroblasts survive well (70–90%), but neither the endothelial cells nor the smooth muscle cells of the aortic tissue associated with the valve survive. Cryopreservation can also be effective for isolated islets of Langerhans, but preservation of islets in bioengineered capsules can be technically difficult. Skin is relatively easy to preserve because of the thin, flat structure of the tissue. It appears that thawing of skin-like products, however, can be technically difficult due to the narrow window for error during warming, outside of which ice growth resulting in tissue damage can occur. In all of these examples, the problems are due to ice formation either within the cells, the extracellular matrix, the capsule, or, as in the case of heart valve endothelium, compression in the lumen of the associated artery.

Vitrification, by contrast, means solidification, as in a glass, without ice crystal formation. The principles of vitrification are well-known. Generally, the lowest temperature a solution can possibly supercool to without freezing is the homogeneous nucleation temperature $T_h$, at which temperature ice crystals nucleate and grow, and a crystalline solid is formed from the solution. Vitrification solutions have a glass transition temperature $T_g$, at which temperature the solute vitrifies, or becomes a non-crystalline solid. Owing to the kinetics of nucleation and crystal growth, it is effectively impossible for water molecules to align for crystal formation at temperatures much below $T_g$. In addition, on cooling most dilute aqueous solutions to the glass transition temperature, $T_h$ is encountered before $T_g$, and ice nucleation occurs, which makes it impossible to vitrify the solution. In order to make such solutions useful in the preservation of biological materials by vitrification, it is therefore necessary to change the properties of the solution so that vitrification occurs instead of ice crystal nucleation and growth. It is also important that all viability and tissue function be maintained by the entire vitrification process.

While it is generally known that high hydrostatic pressures raise $T_g$ and lower $T_h$, vitrification of most dilute solutions by the application of pressure is often impossible or impractical. In particular, for many solutions vitrifiable by the application of pressure, the required pressures cause unacceptably severe injury to unprotected biomaterials during vitrification thereof. While it is also known that many solutes, such as commonly employed cryoprotectants like DMSO, raise $T_g$ and lower $T_h$, solution concentrations of DMSO or similar solutes high enough to permit vitrification typically approach the eutectic concentration and are generally toxic to biological materials.

One type of damage caused by cryoprotectants is osmotic damage. Cryobiologists learned of the osmotic effects of cryoprotectants in the 1950's and of the necessity of controlling these effects so as to prevent damage during the addition and removal of cryoprotectants to isolated cells and tissues. Similar lessons were learned when cryobiologists moved on to studies of whole organ perfusion with cryoprotectants. Attention to the principles of osmosis were essential to induce tolerance to cryoprotectant addition to organs.

Despite efforts to control the deleterious osmotic effects of cryoprotectants, limits of tolerance to cryoprotectants are still observed. There appear to be genuine, inherent toxic effects of cryoprotectants that are independent of the transient osmotic effects of these chemical agents.

Studies by the present inventors and others have examined methods of controlling non-osmotic, inherent toxicity of cryoprotectant agents. The results indicate that several techniques can be effective alone and in combination. These include (a) the use of specific combinations of cryoprotectant whose effects cancel out each other's toxicities; (b) exposure to cryoprotectants in vehicle solutions that are optimized for those particular cryoprotectants; (c) the use of non-penetrating agents that can substitute for a portion of the penetrating agent otherwise needed, thus sparing the cellular interior from exposure to additional intracellular agents; and (d) minimizing the time spent within the concentration range of rapid time-dependent toxicity.

Some of these techniques are in potential conflict with need to control osmotic forces. For example, reduced temperatures also reduce the influx and efflux rate of cryoprotectants, thereby prolonging and intensifying their osmotic effects. Similarly, minimizing exposure time to cryoprotectants maximizes their potential osmotic effects. Thus, there must be a balance reached between the control of osmotic damage and the control of toxicity. Means for obtaining this balance are described in U.S. Pat. No. 5,723,282 to Fahy et al. However, this patent does not describe a particular method to be used for blood vessels, cartilage or other tissues for which vitrification offers a potential technique for improved crypreservation. In addition, this patent does not discuss any protocols for cooling or warming the organ or tissue.

SUMMARY OF THE INVENTION

The present invention is directed to a method for vitrification of tissues, including vascularized tissues and avascular tissues, or organs. The method comprises immersing the tissue or organ in increasing concentrations of cryoprotectant solution at a temperature greater than –5° C. to a cryoprotectant concentration sufficient for vitrification; rapidly cooling the tissue or organ to a temperature between –80° C. and the glass transition temperature ($T_g$); and further cooling the tissue or organ from a temperature above the glass transition temperature to a temperature below the glass transition temperature to vitrify the tissue or organ.

The present invention is also directed to a method for removing a tissue or organ from vitrification in a cryoprotectant solution. The method comprises slowly warning a vitrified tissue or organ in the cryoprotectant solution to a temperature between –80° C. and the glass transition temperature; rapidly warming the tissue or organ in the cryoprotectant solution to a temperature above –75° C.; and reducing the concentration of the cryoprotectant by immersing the tissue or organ in decreasing concentrations of cryoprotectant.

The present invention is also directed to a method for treating tissues or organs such that viability is retained at a high level. For example, for blood vessels, the invention provides that smooth muscle functions and graft patency rate are maintained. In particular, the present invention is directed to a method in which at least 50%, preferably at least 70%, and more preferably greater than 80% of smooth muscle functions and graft patency rate are maintained relative to fresh untreated controls.

DETAILED DESCRIPTION OF PREFERRED EMBODIMENTS

Figure 1:
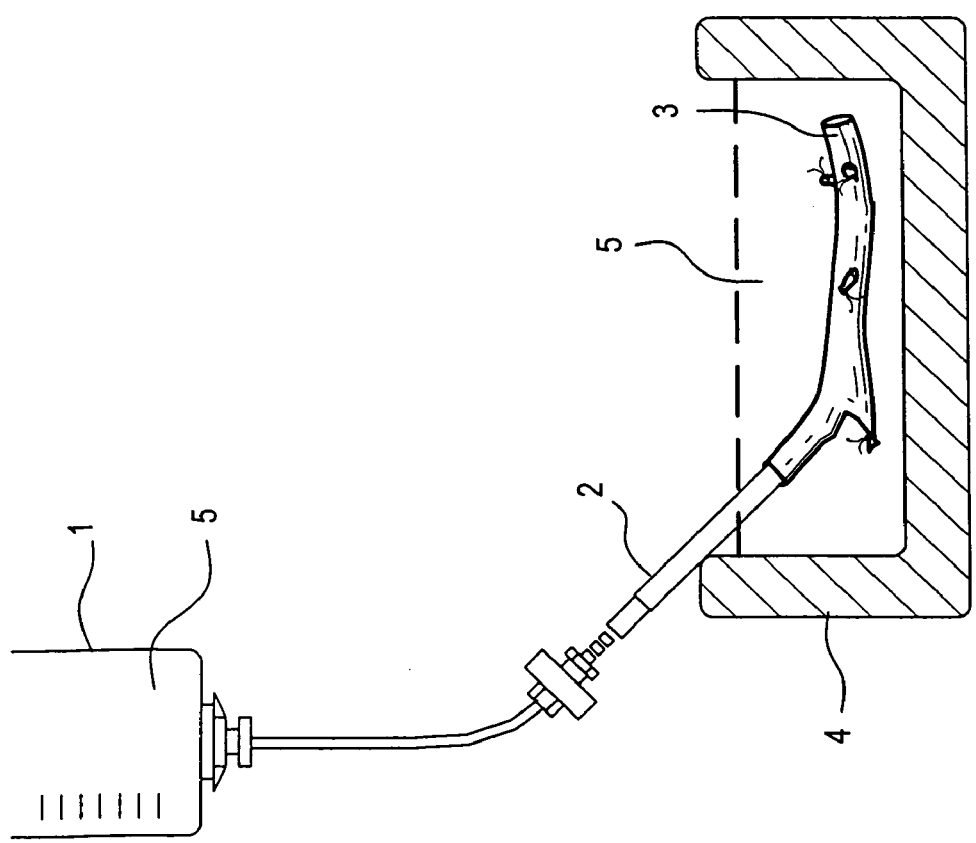
FIG. 1 shows an example of a perfusion system that can be used in the present invention.

The present invention is directed to a method for vitrification of a tissue or organ in a cryoprotectant solution and for subsequently removing the tissue or organ from vitrification. "Tissue or organ" is used herein to refer to any natural or engineered biological tissue or organ, including, but not limited to, vascularized tissues and avascular tissues, including vascular tissue, such as blood vessels, musculoskeletal tissue, such as cartilage, menisci, muscles, ligaments and tendons, skin, cardiovascular tissue, such as heart valves and myocardium, neuronal tissue, periodontal tissue, glandular tissue, organ tissue, islets of Langerhans, cornea, ureter, urethra, breast tissue, and organs, such as pancreas, bladder, kidney, breast, liver, intestine, heart and sections or pieces thereof. "Blood vessel" is used herein to refer to any biological tube conveying blood. Thus, the phrase refers inter alia to an artery, capillary, vein, sinus or engineered construct.

As used herein, the term "transplantation" refers to any type of transplantation or implantation whether or not autologous, homologous or heterologous, and whether or not it is performed directly or subsequent to further processing of the tissue or organ.

As used herein, the term "vitrification" refers to solidification without ice crystal formation. As used herein, a tissue is vitrified when it reaches the glass transition temperature (Tg). The process of vitrification involves a marked increase in viscosity of the cryoprotectant solution as the temperature is lowered such that ice nucleation and growth are inhibited. In practice, vitrification or vitreous cryopreservation may be achieved even in the presence of a small, or restricted amount of ice, which is less than an amount that causes injury to the tissue.

As used herein, the "glass transition temperature" refers to the glass transition temperature of a solution under the conditions at which the process is being conducted. In general, the process of the present invention is conducted at physiological pressures. However, higher pressures can be used as long as the tissue or organ is not significantly damaged thereby.

As used herein, "physiological pressures" refer to pressures that tissues or organs undergo during normal function. The term "physiological pressures" thus includes normal atmospheric conditions, as well as the higher pressures that various tissues, such as vascular tissues and blood vessels undergo under diastolic and systolic conditions.

As used herein, the term "perfusion" means the flowing of a fluid through the tissue or organ. Techniques for perfusing organs and tissues are discussed in, for example, U.S. Pat. No. 5,723,282 to Fahy et al., which is incorporated herein in its entirety.

As used herein, the term "cryoprotectant" means a chemical that minimizes ice crystal formation in a tissue or organ when the tissue or organ is cooled to subzero temperatures and results in an increase in viability after warming, in comparison to the effect of cooling without cryoprotectant.

As used herein, "approximate osmotic equilibration" means that there is no more than a 10% difference between the intracellular and extracellular solute concentrations. A difference of no more than 10% means, for example, that, if the extracellular concentration is 4M, the intracellular solute concentration is between 3.6 and 4.4M. Preferably, there is no more than a 5% difference between the intracellular and extracellular concentrations.

Vitrification can be achieved using a variety of cryoprotectant mixtures and cooling/warming conditions. The key variables should be optimized for each particular cell or tissue type and sample size. The choice of cryoprotectant mixtures and the equilibration steps necessary for cryoprotectant addition and removal without undue osmotic shock should be optimized based upon measured kinetics of cryoprotectant permeation in tissue samples. Cryosubstitution can also be employed to verify that ice-free preservation has been achieved for a given protocol.

In the method of the present invention, the tissue or organ is immersed in increasing concentrations of cryoprotectant solution at a temperature greater than −5° C. Blood vessels and organs and tissues containing blood vessels may be perfused, instead of, or in conjunction with, immersion. The temperature is preferably between 0° C. and 15° C., more preferably between 0° C. and 10° C. Preferably, the tissue or organ is also perfused with the increasing concentrations of cryoprotectant.

The increase in concentration is preferably conducted in a step-wise manner. That is, cryoprotectant is added to the extracellular solution to achieve a particular concentration of cryoprotectant. After this concentration level is obtained, the concentration of the solution is then substantially maintained for a period of time. In particular, the concentration level is generally maintained for a sufficient time to permit approximate osmotic equilibration of the tissue or organ in the solution. To obtain approximate osmotic equilibration, the concentration level is generally maintained for at least 10 minutes. In a preferred embodiment, the concentration level is maintained for at least 15 minutes. This process is repeated as many times as necessary, with the final concentration being sufficient for vitrification at physiological pressures, particularly under normal atmospheric conditions. In addition, the tissue or organ is generally maintained at each concentration level for no more than an hour, preferably for no more than 30 minutes.

In general, the tissue or organ is first immersed in a cryoprotectant-free solution. The tissue or organ may also be perfused with the cryoprotectant-free solution. This cryoprotectant-free solution can be any type of solution that maintains cellular integrity under in vitro conditions as typified by synthetic physical buffers at normal temperatures, and organ preservation solutions at hypothermic temperatures. Most typically, the initial cryoprotectant-free solution will be the same as the vehicle solution used to add and remove cryoprotectants in the tissue or organ. For example, the cryoprotectant-free solution can be a Euro-Collins solution, which is an aqueous solution described in Table 1 below.

TABLE 1

Euro-Collins*

| Compound | mM | g/l |
|---|---|---|
| Dextrose | 194 | 34.96 |
| $KH_2PO_4$ | 15 | 2.06 |
| $K_2HPO_4$ | 42 | 7.40 |
| KCl | 15 | 1.12 |
| $NaHCO_3$ | 10 | 0.84 |

*pH = 7.4
*milliosmolality = 350–365 milliosmolal

Other examples of suitable aqueous solutions are discussed in Tables 2 and 3 below.

TABLE 2

Modified RPS-2

| Compound | mM | g/l |
|---|---|---|
| Dextrose | 180 | 32.43 |
| $K_2HPO_4$ | 7.2 | 1.25 |
| KCl | 28.2 | 2.11 |
| $NaHCO_3$ | 10 | 0.84 |
| Glutathione | 5 | 1.53 |
| Adenine HCl | 1 | 0.17 |
| $CaCl_2$ | 1 | 0.111 |
| $MgCl_2$ | 2 | 0.407 |

(Note: RPS-2 ™ solution is modified RPS-2 without $CaCl_2$ and also without $MgCl_2$)

TABLE 3

| Modified UW Solution #1 | | | Modified UW Solution #2 | | |
|---|---|---|---|---|---|
| Compound | mM | g/l | Compound | mM | g/l |
| $NaH_2PO_4.H_2O$ | 25 | 3.45 | $NaH_2PO_4.H_2O$ | 25 | 3.45 |
| K gluconate | 100 | 23.42 | K gluconate | 100 | 23.42 |
| Mg gluconate | 1 | 0.21 | Mg gluconate | 1 | 0.21 |
| glucose | 5 | 0.90 | glucose | 15 | 2.70 |
| glutathione | 3 | 0.92 | glutathione | 3 | 0.92 |
| adenosine | 5 | 1.34 | adenosine | 5 | 1.34 |
| HEPES | 10 | 2.38 | HEPES | 10 | 2.38 |
| adenine (hydrochloride) | 1 | 0.17 | adenine (hydrochloride) | 1 | 0.17 |
| ribose | 1 | 0.15 | ribose | 1 | 0.15 |
| $CaCl_2$ | 0.05 | 0.0056 | $CaCl_2$ | 0.05 | 0.0056 |
| HES(g) | — | 50 | — | — | — |

(Note: Modified UW Solution #2 does not contain HES but contains more glucose than modified UW Solution #1)

After being immersed in a cryoprotectant-free solution, the tissue or organ is immersed in a solution containing cryoprotectant with or without perfusion. (An advantage of the present invention is that perfusion is not necessarily required.) A cryoprotectant concentration sufficient for vitrification generally contains from 6.0 to 9.5M cryoprotectant, preferably from 7 to 9M cryoprotectant, more preferably from 8 to 9M cryoprotectant. The cryoprotectant solution may contain any combination of cryoprotectants sufficient for vitrification. Cryoprotectants include, but are not limited to, dimethyl sulfoxide, formamide, 1,2-propanediol, 2,3-butanediol, glycerol, ethylene glycol, n-dimethyl formamide and 1,3-propanediol.

Impermeable cryoprotectant agents such as polyvinylpyrrolidone or hydroxyethyl starch may be more effective at protecting biological systems cooled at rapid rates. Such agents are often large macromolecules, which effect the properties of the solution to a greater extent than would be expected from their osmotic pressure. Some of these non-permeating cryoprotectant agents have direct protective effects on the cell membrane. However, the primary mechanism of action appears to be the induction of extracellular glass formation. When such cryoprotectants are used in extremely high concentrations, ice formation may be eliminated entirely during cooling to and warming from cryogenic temperatures. Impermeable chemicals with demonstrated cryoprotective activity include agarose, dextrans, glucose, hydroxyethylstarch, inositol, lactose, methyl glucose, polyvinylpyrrolidone, sorbitol, sucrose and urea.

In a particular embodiment of the present invention, the cryoprotectant solution contains dimethyl sulfoxide, formamide, and 1,2-propanediol. For example, the cryoprotectant solution may be a solution called VS55. VS55 is a solution containing 24.2% w/v (3.1M) dimethyl sulfoxide, 16.8% w/v (2.2M) 1,2-propanediol, and 14.0% w/v (3.1M) formamide in a vehicle solution, such as Euro-Collins solution. Thus, the solution contains about 55% w/v cryoprotectant or 8.4M cryoprotectant. The amount of dimethyl sulfoxide may be varied from 20 to 30% w/v. Similarly, the amount of 1,2-propanediol and formamide may each be varied from about 10 to 20% w/v. However, the total amount of cryoprotectant in the full strength solution should be between 45% w/v to 60% w/v, preferably from about 50% w/v to 55% w/v.

VS55 may also be modified with conventional cryoprotectants and/or natural or synthetic ice-blocking molecules, for example, acetamide, agarose, alginate, alanine, albumin, ammonium acetate, anti-freeze proteins, butanediol, chondroitin sulfate, chloroform, choline, cyclohexanediols, cyclohexanediones, cyclohexanetriols, dextrans, diethylene glycol, dimethyl acetamide, dimethyl formamide, erythritol, ethanol, ethylene glycol, ethylene glycol monomethyl ether, glucose, glycerol, glycerophosphate, glyceryl monoacetate, glycine, glycoproteins, hydroxyethyl starch, inositol, lactose, magnesium chloride, magnesium, sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and/or xylose.

In addition, in further preferred embodiments of the invention, 1,2-propanediol may be replaced by similar concentrations of 2,3-butanediol. Similarly, dimethyl sulfoxide may be replaced by similar concentrations of glycerol or ethylene glycol or combinations thereof.

The vehicle for the cryoprotectant solution may be any type of solution that maintains cellular integrity under in vitro conditions. In particular, the vehicle generally comprises slowly penetrating solutes. In VS55, the vehicle solution is a Euro-Collins solution containing 10 mM HEPES. HEPES is included as a buffer and may be included in any effective amount. In addition, other buffers, as well as no buffer, may be used. Alternative vehicles include, but are not limited to, the solutions discussed in Tables 2 and 3 above.

The final concentration of the perfusion solution is sufficient to vitrify the tissue or organ. However, as discussed above, the concentration of the solution is gradually increased to achieve this level, preferably in a step-wise manner. In particular, cryoprotectant is added to achieve a particular plateau, which is maintained for a sufficient time to achieve approximate osmotic equilibration, in particular for at least 10 minutes and preferably for about 15 minutes. Then, further cryoprotectant is added to increase the cryoprotectant concentration, which may or may not be a level sufficient for vitrification. If not, after maintaining the concentration for sufficient time to achieve approximate osmotic equilibration, further cryoprotectant is added in one or more steps to achieve a concentration sufficient for vitrification.

In a preferred embodiment of the invention, there are four cryoprotectant concentration plateaus before reaching the concentration sufficient for vitrification. In this preferred embodiment, there are thus six steps, the first step using a cryoprotectant-free solution, which is followed by four increasing cryoprotectant concentration plateaus and then a cryoprotectant concentration sufficient for vitrification. In a particularly preferred six step embodiment, in step 1, no cryoprotectant is used; in step 2, 5 to 20%, preferably 10 to 15%, of the final cryoprotectant concentration is used; in step 3, 15 to 35%, preferably 20 to 30%, of the final cryoprotectant concentration is used; in step 4, 40 to 60%, preferably 45 to 55%, of the final cryoprotectant concentration is used; in step 5, 65 to 85%, preferably 70 to 80%, of the final cryoprotectant concentration is used; and in step 6, the final cryoprotectant concentration, which is sufficient for vitrification, is used. Each cryoprotectant concentration step is maintained for a sufficient time to achieve approximate osmotic equilibration. In a further preferred embodiment, the tissue or organ is perfused with the solution at each step.

After the tissue or organ has been immersed in a solution containing a concentration of cryoprotectant sufficient for vitrification, the tissue or organ, which is maintained in a solution containing a concentration of cryoprotectant sufficient for vitrification, is rapidly cooled to a temperature between −80° C. and the glass transition temperature. The rapid cooling rate may be from 2.5 to 100° C. per minute. The rapid cooling rate is generally at least 15, 20, 25 or 30° C. per minute. The average cooling rate during this step is preferably from 10 to 80° C., more preferably from 30–60° C. per minute, even more preferably from 35–50° C. per minute, and even further more preferably from 40–45° C. per minute. The temperature to which the tissue or organ is cooled during this rapid cooling process is preferably between −90 and −110° C., more preferably between −95 and −105° C.

After the tissue or organ undergoes this rapid cooling process, the tissue or organ then undergoes a slow cooling process in which the tissue or organ is cooled at an average rate less than 30° C. per minute, preferably at an average rate less than 10° C. per minute from a temperature above the glass transition temperature to a temperature below the glass transition temperature to vitrify the tissue or organ. The cooling process is preferably conducted at an average rate less than 5° C. per minute. Preferably, the rate of cooling during this entire step does not increase above 30° C. per minute, more preferably the rate of cooling does not increase above 10° C. per minute and even more preferably the rate of cooling does not increase above 5° C. per minute. The glass transition temperature is generally about −120° C. to −135° C. under normal atmospheric conditions. The tissue or organ can then be stored for long period of time at a temperature below the glass transition temperature.

The first cooling rate is generally faster than the second cooling rate; however, in embodiments, the two cooling rates can be the same.

In an embodiment of the invention, the slow cooling rate is achieved by changing the environment in which the container containing the solution is placed. In a particular embodiment, the rapid cooling rate is achieved by placing the container in a liquid, such as 2-methylbutane, that has been pre-cooled to a temperature below −100° C., preferably near or below the glass transition temperature of the solution to be cooled. Then, to achieve the slow cooling rate, the container is removed from the liquid and cooled in a gaseous environment at a temperature below the glass transition temperature.

The present invention is also directed to a method for removing a tissue or organ from vitrification in a cryoprotectant solution with or without perfusion. The method comprises slowly warming a vitrified tissue or organ in the cryoprotectant solution to a temperature between −80° C. and the glass transition temperature. The slow warming rate is generally below 50° C. per minute. In addition, the average warming rate during this stage is generally from 20–40° C. per minute, preferably from 25–35° C. per minute. In addition, the temperature to which the vitrified tissue or organ is slowly warmed is preferably between −90 and −110° C., more preferably between −95 and −105° C.

After the tissue or organ has undergone this slow warming process, the tissue or organ is then rapidly warmed to a temperature above −75° C. The temperature should be sufficiently high that the solution is sufficiently fluid that the tissue or organ can be removed therefrom. The rapid warming process is generally conducted at a rate above 80° C. per minute, preferably above 100° C. per minute. The average warming rate during this step is preferably from 200–300° C. per minute, more preferably from 215–250° C. per minute. The tissue or organ is preferably warmed in this process to a temperature above −75° C., such as above −35° C. However, in a further embodiment of the invention, the tissue or organ is warmed in this step to a temperature above −5° C., preferably between −5° C. and +5° C.

In an embodiment of the invention, the rapid warming rate is achieved by changing the environment in which the container containing the solution is placed. In a particular embodiment, the slow warming rate is achieved by placing the container in a gaseous environment at a temperature above the temperature at which the tissue or organ has been stored. Then, to achieve the rapid warming rate, the container is placed in a liquid, such as an aqueous solution of, for example, dimethyl sulfoxide (DMSO), at a temperature above −75° C., preferably above 0° C., and more preferably at normal atmospheric temperatures.

After the tissue or organ has been warmed to a temperature above −65° C., the concentration of the cryoprotectant in the solution is gradually reduced. Preferably, the cryoprotectant concentration is reduced in a step-wise manner. In an embodiment of the invention, decreasing cryoprotectant solutions are achieved by immersing the tissue or organ in a series of decreasing cryoprotectant concentration solutions to facilitate elution of cryoprotectants from the tissue or organ. The tissue or organ may also be perfused with the solutions. The solutions are generally at a temperature above −15° C., preferably between −15 and +15° C., more preferably between 0° C. and 10° C.

The cryoprotectant concentration is preferably reduced to achieve a particular plateau, which is maintained for a sufficient time to achieve approximate osmotic equilibration, in particular for at least 10 minutes and preferably for about 15 minutes. Then, the cryoprotectant concentration is further reduced, which may or may not provide for a cryoprotectant-free solution. If not, after maintaining the concentration for sufficient time to achieve approximate osmotic equilibration, the cryoprotectant concentration is again further reduced in one or more steps to eventually provide a cryoprotectant-free solution. In addition, the tissue or organ is generally immersed in each solution for no longer than an hour, preferably no longer than 30 minutes.

To decrease the cryoprotectant concentration, the cryoprotectant solution may be mixed with a solution of a type similar to the cryoprotectant-free solution utilized in adding cryoprotectant to the tissue or organ. The solution preferably comprises at least one osmotic buffering agent.

The vitrification methods of the present invention typically result in a greater number or percentage of viable cells in a tissue or organ sample as compared to conventional cryopreservation techniques involving freezing. The methods of the present invention generally result in tissue or organ samples having at least 50% viable cells. In embodiments, the methods of the present invention result in tissue or organ samples having at least 60% viable cells, for example at least 80% viability, such as at least 90% viability. The present invention can also result in at least 70%, preferably at least 80%, of cell functions and graft functions being maintained relative to fresh untreated controls.

As used herein, "osmotic buffering agent" means a low or high molecular weight non-penetrating extracellular solute that counteracts the osmotic effects of the greater intracellular than extracellular concentrations of cryoprotectant during the cryoprotectant efflux process.

As used herein "non-penetrating" means that the great majority of molecules of the chemical do not penetrate into the cells of the tissue or organ but instead remain in the extracellular fluid of the tissue.

As used herein, "low molecular weight osmotic buffering agents" have a relative molecular mass of 1,000 daltons or less. Low molecular weight osmotic buffering agents include, but are not limited to, maltose, potassium and sodium fructose 1,6-diphosphate, potassium and sodium lactobionate, potassium and sodium glycerophosphate, maltopentose, stachyose, mannitol, sucrose, glucose, maltotriose, sodium and potassium gluconate, sodium and potassium glucose 6-phosphate, and raffinose. In a preferred embodiment, the low molecular weight osmotic buffering agent is at least one of mannitol, sucrose and raffinose.

As used herein, "high molecular weight cryoprotectant and osmotic buffering agents" generally have a relative molecular mass of from greater than 1,000 to 500,000 daltons. High molecular weight osmotic buffering agents include, but are not limited to, hydroxyethyl starch (HES), polyvinylpyrrolidone (PVP), potassium raffinose undecaacetate (>1,000 daltons) and Ficoll (greater than 1,000 to 100,000 daltons). In a preferred embodiment, the high molecular weight osmotic buffering agent is HES, more preferably having a molecular weight of about 450,000.

The cryoprotectant-free solution preferably contains less than about 500 mM of an osmotic buffering agent, more preferably from about 200 to 400 mM osmotic buffering agent. As the osmotic buffering agent, preferably a low molecular weight osmotic buffering agent is used. Most preferably, the low molecular weight osmotic buffering agent is mannitol.

In a particularly preferred embodiment, the cryoprotectant is removed in seven steps. In the preferred embodiment, in step 1, the cryoprotectant concentration is 40 to 60%, preferably 45 to 55%, of the cryoprotectant concentration used for vitrification; in a step 2, the cryoprotectant concentration is 30 to 45%, preferably 35 to 40%, of the cryoprotectant concentration used for vitrification; in step 3, the cryoprotectant concentration is 15 to 35%, preferably 20 to 30%, of the cryoprotectant concentration used for vitrification; in step 4, the cryoprotectant concentration is 5 to 20%, preferably 10 to 15%, of the cryoprotectant concentration used for vitrification; and in step 5, the cryoprotectant concentration is 2.5 to 10%, preferably 5 to 7.5%, of the cryoprotectant concentration used for vitrification. In these steps, the remainder of the solution is a cryoprotectant-free solution containing osmotic buffering agent. In step 6, essentially all of the cryoprotectant is removed. However, the osmotic buffering agent is retained. In step 7, the osmotic buffering agent is removed. Alternatively, steps 6 and 7 can be combined in a single step. That is, the osmotic buffering agent can be removed at the same time as the remainder of the cryoprotectant. In addition, if no osmotic buffering agent is used or if it is not removed, step 7 can be eliminated. Each of these concentration steps is maintained for a sufficient time to achieve approximate osmotic equilibration.

The temperature of the series of solutions is generally above −15° C., preferably between −15 and +15° C., and more preferably between 0° C. and +10° C. When step 1 is begun, the tissue or organ is at a temperature above −75° C., preferably above −65° C. Thus, if the temperature of the tissue or organ is below the temperature of the solution in which it is immersed in step 1, the tissue or organ is further warmed to a temperature above −15° C. during step 1 of the cryoprotectant removal.

The tissue or organ may be further processed before or after vitrification and/or devitrification. For example, tissues or organs can be revitalized before and/or after vitrification and devitrification by perfusion processes such as those described in U.S. patent application Ser. No. 09/645,525, the entire contents of which are hereby incorporated by reference. Tissues or organs can be genetically engineered before vitrification, and/or can be re-engineered after devitrification, for example by the cartilage digestion and cellular proliferation processes described in Binette F, McQuaid D P, Haudenschild D R, Yaeger P C, McPherson J M, Tubo R, "Expression of a Stable Articular Cartilage Phenotype without Evidence of Hypertrophy by Adult Human Articular Chondrocytes In Vitro", *J Orthop Res*, Vol. 16, No. 2, 1998, and Stone B B, DeFranzo B E, DiCesare C, Rapko S M, Brockbank K G M, Wolfrum J M, Wrenn C A, Grosman J D, "Cryopreservation of Human Articular Cartilage for Autologous Chondrocyte Implantation" presented at 35$^{th}$ Annual Meeting of Society for Cryobiology, July 1998, the entire contents of which are hereby incorporated by reference. Alternatively, tissues or organs can be vitrified substantially directly after harvest and/or transplanted substantially directly after devitrification.

EXAMPLES

Example 1

Blood Vessels

The external jugular vein was obtained from New Zealand white rabbits. The distal site of each vein segment above the bifurcation was cannulated in situ with a silicone tube. The proximal site was left open for fluid outflow. The vein segments, which were about 40–60 mm long, were perfused at 0° C. to 4° C.

To perfuse the veins, the perfusion system of FIG. 1 was used. The perfusion system comprises a reservoir 1 (a 60 cc syringe) containing perfusion solution 5 connected to the cannula 2 with a 3-way stopcock. The reservoir 1 was adjusted to physiologic pressure. The vein 3 was placed in a petri dish 4 (Dia.×H, 50×15 mm) containing perfusion solution 5. The perfusion solution 5 in both reservoir 1 and petri dish 4 was the same and was pre-cooled (0° C.–4° C.) and the petri dish 4 was placed in ice (0° C.–4° C.) during the perfusion process.

The vitrification solution used was VS55. The full strength VS55 solution was introduced in six serial steps. In the first step, the blood vessels were perfused with Euro-Collins solution, which is the carrier of VS55. In steps two to five, respectively, the amount of full strength VS55 in the solution was as follows: 1/8 VS55, 2/8 VS55; 4/8 VS55; and 6/8 VS55. In each case, the remainder of the solution was Euro-Collins solution. In the sixth step, the perfusion solution was full strength VS55. Exposure at each step was for 15 minutes.

Figure 2:
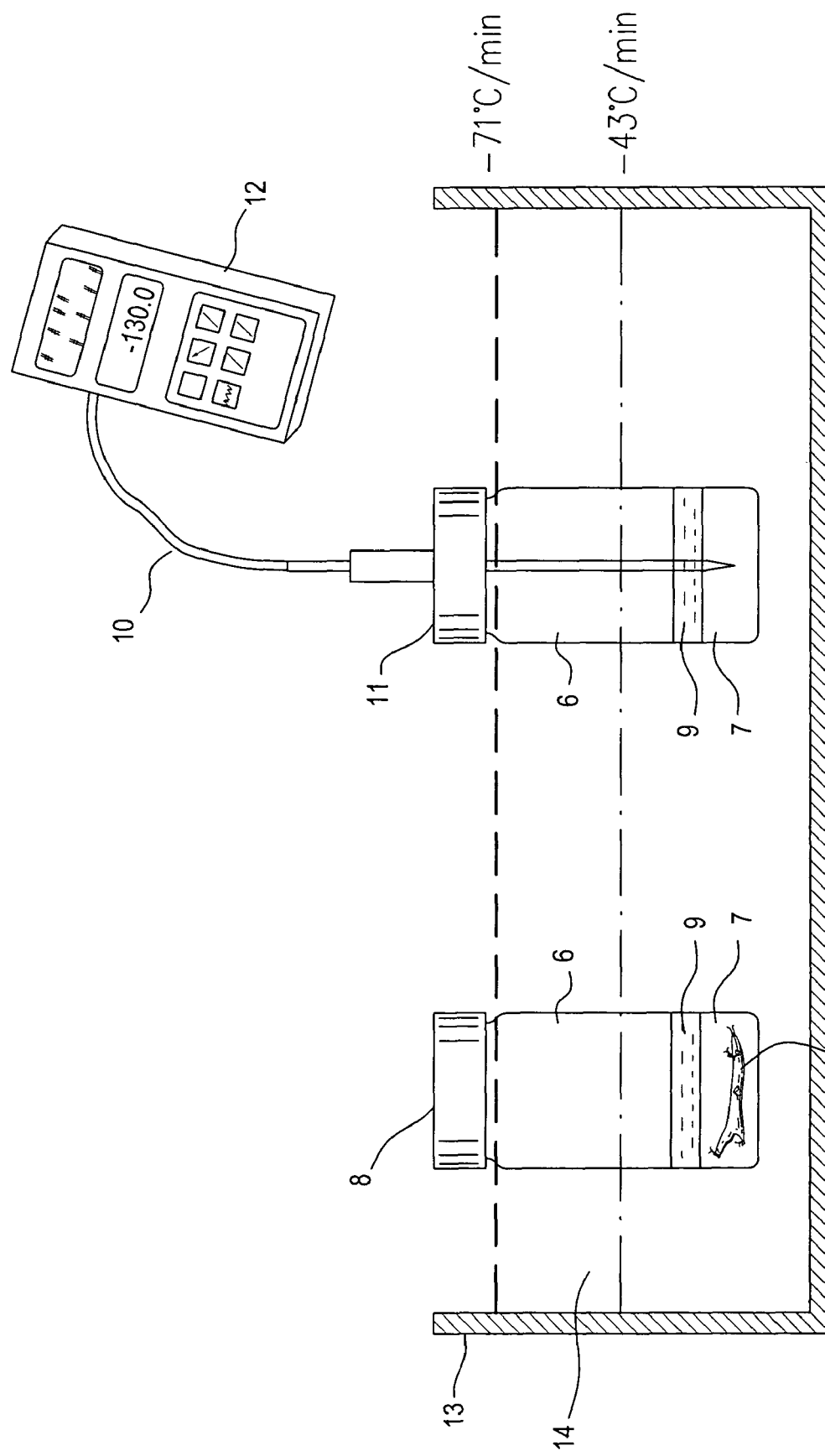
FIG. 2 shows a device that can be used for rapidly cooling tissues or organs.

After addition of the vitrification solution, the vein segments were rapidly cooled using the device demonstrated in FIG. 2. The vein segments 3, together with the silicone tube, were placed in a glass scintillation vial 6 (Dia.×H, 25×60 mm) containing 1 ml of pre-cooled full strength VS55 solution 7 to form the sample 8. The top of the vitrification solution 7 was covered with 0.7 ml of 2-methylbutane 9 (isopentane, freezing point: −160° C., density: 0.62) at 0° C. to 4° C. to prevent direct contact with air. A thermocouple 10 was inserted into a dummy sample 11 of the vitrification solution 7, and its output was monitored on a digital thermometer 12. Temperature was recorded throughout the cooling process.

Figure 3:
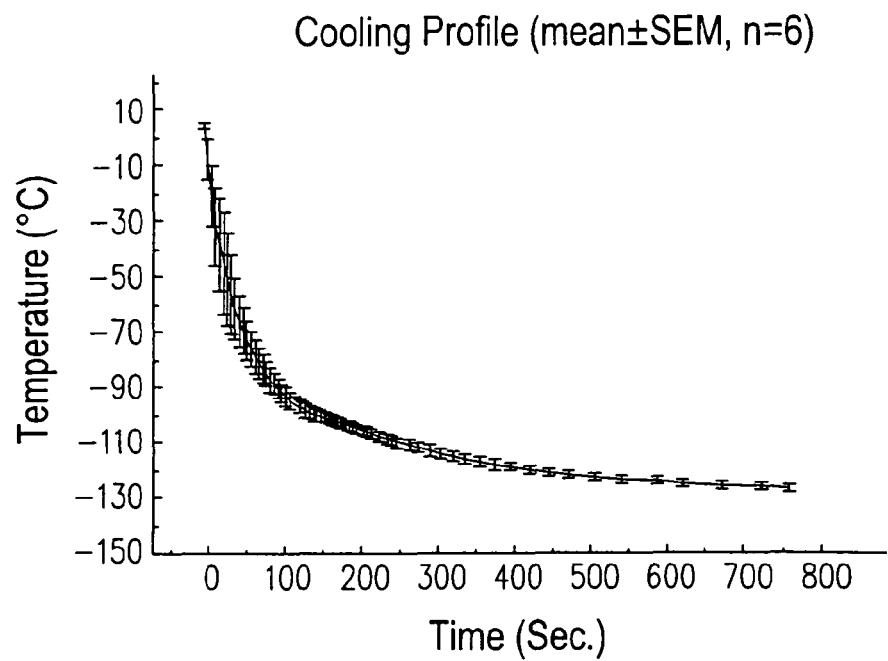
FIG. 3 shows the cooling profile generated by placing the glass scintillation vial 30 mm deep in precooled 2-methylbutane and then in cold air using the device of FIG. 2.

The cooling apparatus was set up inside a −135° C. freezer. The cooling rates were adjusted by placing the sample in a container 13 containing precooled 2-methylbutane 14. The cooling rates could be varied depending on the depth the vial was placed in 2-methylbutane (30 mm generate a cooling rate of 43° C./min; 60 mm generate cooling rate 71° C./min). By this technique, the samples were cooled rapidly (average rate=43±2° C./min) to −100° C. The samples were then slowly cooled (average rate=3±0.2° C./min) to −135° C. by taking the sample out of the container 13 of 2-methylbutane 14 and allowing the air in the −135° C. freezer to complete the cooling process. FIG. 3 shows the cooling profile using the technique of placing the glass scintillation vial 30 mm deep in precooled (−135° C.) 2-methylbutane. The sample was then stored in the −135° C. freezer for at least 24 hours.

Figure 4:
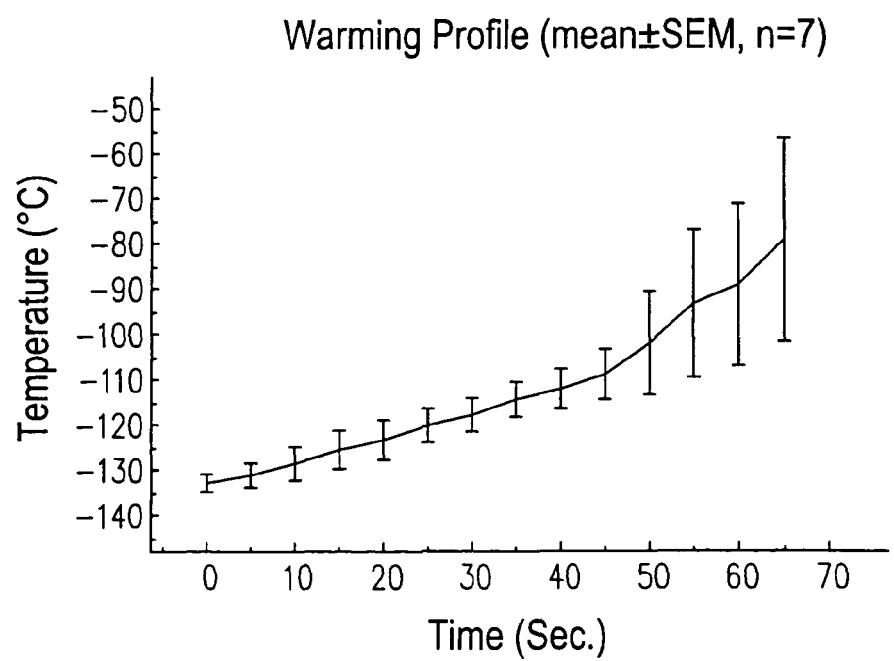
FIG. 4 shows the warming profile generated by placing the glass scintillation vial in cold air and then in a mixture of 30% DMSO/$H_2O$ at room temperature.

After being stored for 24 hours, the veins were rewarmed in two stages, slow warming to −100° C. (average rate=30±2° C./min) and rapid warming to −65° C. (average rate=225±15° C./min). The slow warming rate was created by taking the sample to the top of the −135° C. freezer and the fast warming rate was generated by placing the glass vial in a mixture of 30% DMSO/H$_2$O at room temperature. FIG. 4 shows the warming profile using this technique.

The VS55 vitrification solution was then removed in seven steps, using the perfusion system of FIG. 1. The perfusion solution 5 in both reservoir 1 and petri dish 4 was the same and was pre-cooled (0° C.–4° C.) and the petri dish 4 was placed in ice (0° C. to 4° C.) during the perfusion process. Thus, during the first step the blood vessel is further warmed to a temperature between 0° C. and 4° C.

In all of the steps except the last step, the solution contained, in addition to the cryoprotectant solution, 400 to 200 mM mannitol. In steps one to five, the amount of full strength VS55 in the solution was as follows: 4/8 VS55; 3/8 VS55; 2/8 VS55; 1/8 VS55; and 0.5/8 VS55, with the remainder of the solution being a mannitol-containing Euro-Collins solution (The 4/8 strength VS55 solution contained 400 mM mannitol and the cryoprotectant-free Euro-Collins solution that was mixed therewith to form the lower cryoprotectant concentration solutions contained 200 mM mannitol. Thus, as the amount of VS55 was decreased, the amount of mannitol was decreased between 400 and 200 mM.) In step six, Euro-Collins solution containing 200 mM mannitol was used. In step 7, a Euro-Collins solution that did not contain mannitol was used. Exposure at each step was for 15 minutes.

Figure 5:
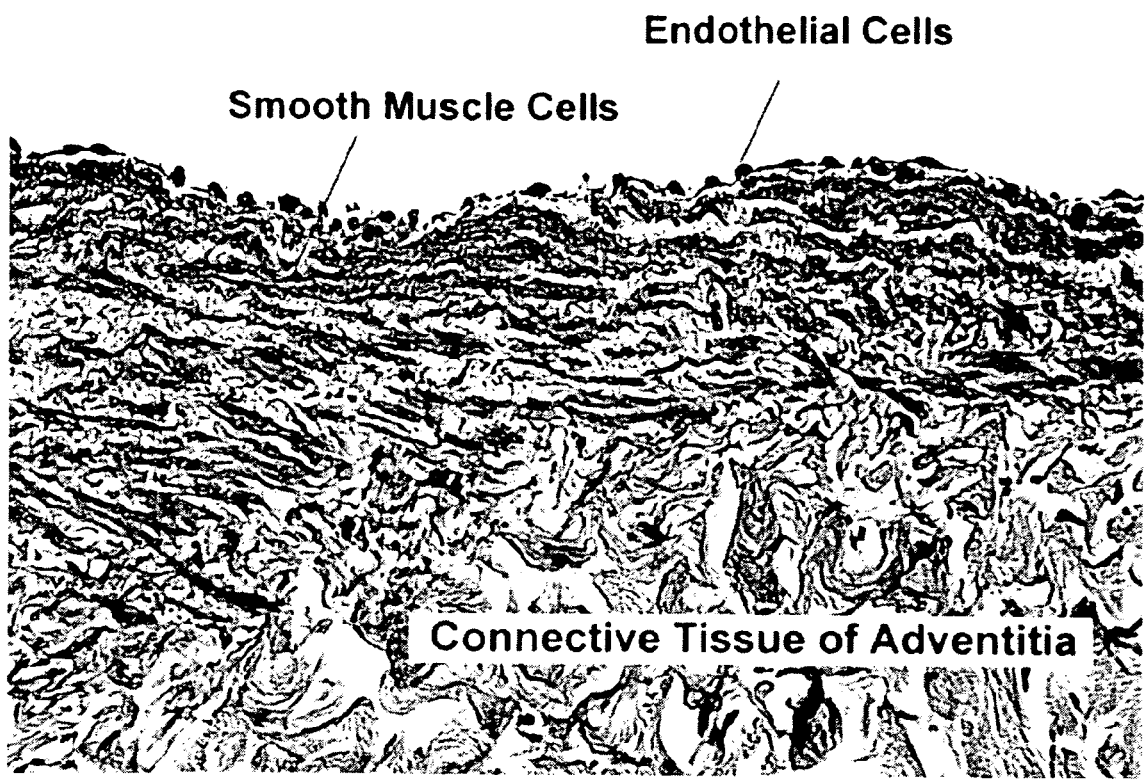
FIG. 5 shows the structural integrity of vein segments following preservation by vitrification.

The morphology studies showed that the structural integrity of vein segments was preserved following vitrification. FIG. 5 demonstrates a histological section of a vitrified rabbit jugular vein showing intact morphological features, including endothelial cells, smooth muscle and the connective tissue of the adventitia.

Vein graft implantation experiments demonstrate the viability of the vein segments after vitrification as compared to fresh autologous veins into the carotid position as a control procedure. New Zealand white rabbits (average weight 2.0 to 2.5 kg) underwent a right common carotid interposition bypass graft. The fresh, or vitrified, reversed ipsilateral external jugular veins were used as syngeneic grafts. Animals were sacrificed at either two or four weeks after implantation. Vein grafts were harvested for histology studies.

Operative Procedure

Anesthesia was induced in New Zealand white rabbits with an injection of a mixture of ketamine hydrochloride (60 mg/kg) and xylazine (6 mg/kg) and maintained in intubated animals using isoflurane delivered in oxygen. A single-dose antibiotic prophylaxis in the form of enrofloxacin (5 mg/kg) was given intramuscularly at the time of induction. The operation was performed with an operating microscope under sterile conditions. After exposure through a right longitudinal neck incision, the right external jugular vein was identified; its branches were cauterized and then removed. Fresh veins were implanted immediately. Vitrified veins were rewarmed in the laboratory and transported to the operation room in DMEM medium on ice.

Figure 6:
FIGS. 6A–F show fresh and vitrified grafts at implantation, after perfusion, fixation and removal, and after graft dissection.
Figure 6:
Figure 6:
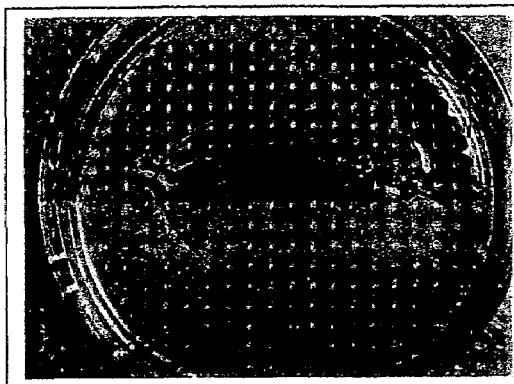
Figure 6:
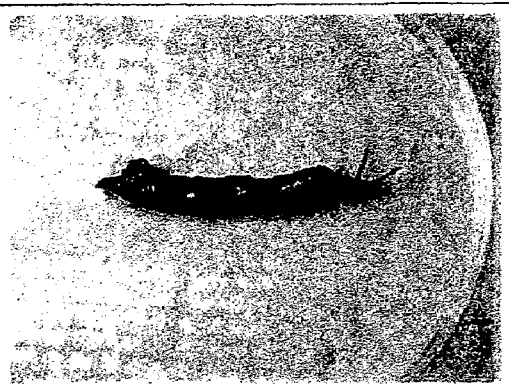
Figure 6:
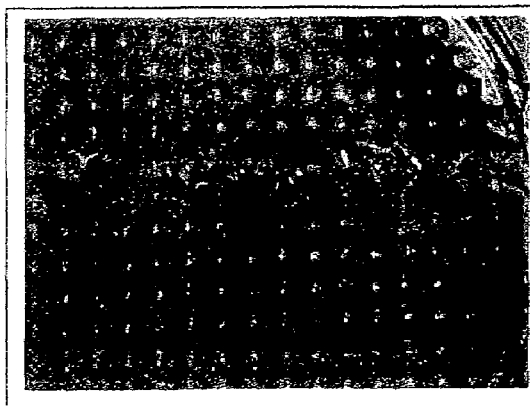
Figure 6:
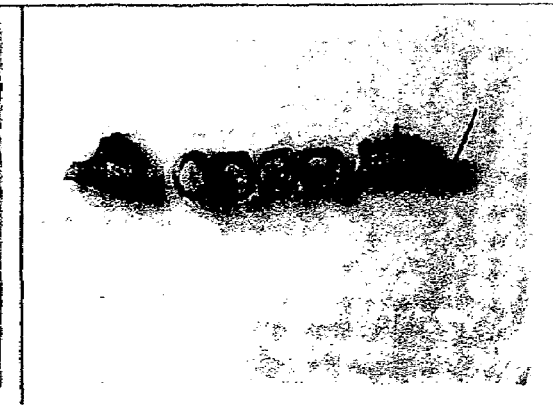

At the time of implantation, the right common carotid artery was identified and dissected. Heparin (200 IU/kg) was administered intravenously. A proximal longitudinal arteriotomy was made, and one end of the reversed jugular vein was anastomosed to the artery end-to-side with a continuous 8–0 microvascular prolene suture. The distal anastomosis was performed similarly (FIG. 6, A-B). Throughout the procedure, care was taken to avoid unnecessary instrumentation of the vein graft. The right common carotid was ligated and divided between the two anastomoses with 4–0 silk ligatures. Hemostasis was achieved, and the wound was subsequently closed in layers.

During recovery, analgesic (buprenorphine 0.05 mg/kg, S.C.) was provided as necessary. Animals were observed daily for signs of infection, illness, injury, or abnormal behavior. Sick or injured animals were referred immediately for veterinary care or euthanized. At the time of graft harvest, under the same anesthetic regimen described above, the original incision was reopened and both the vein grafts and the non-operated contralateral veins were isolated. Following heparinisation, the vein grafts and contralateral controls were perfusion fixed in situ at 80 mm Hg (FIG. 6, C-D). Grafts were perfused with a standardized initial infusion of lactated Ringer's solution followed by 2% glutaraldehyde made up in 0.1M cacodylate buffer supplemented with 0.1M sucrose to give an osmolality of approximately 300 mOsm/kg. After immersion in fixative for 24–48 hours, the graft was divided into a proximal, middle and distal parts (FIG. 6, E-F). Cross-sections from the central region and longitudinal-sections from proximal and distal anastomosis regions were taken for histology studies.

Graft Patency

Using these techniques, 10 fresh grafts have been harvested, and 9 grafts were patent two or four weeks post-operatively. One four-week graft that was not patent was not attributable to technical complications. In this study, we achieved similar patency results to those obtained by other investigators using the same surgical procedures. In addition, 12 vitrified grafts were harvested, and 11 grafts remained patent. The failed graft was found at the time of harvest. It was due to a surgical error made in the proximal anastomosis that blocked blood flow. This study demonstrated similar patency rates in fresh and vitrified autologous vein grafts. The study also included one allograft vein segment that was patent 2-weeks after explantation.

Histology Study

Figure 7:
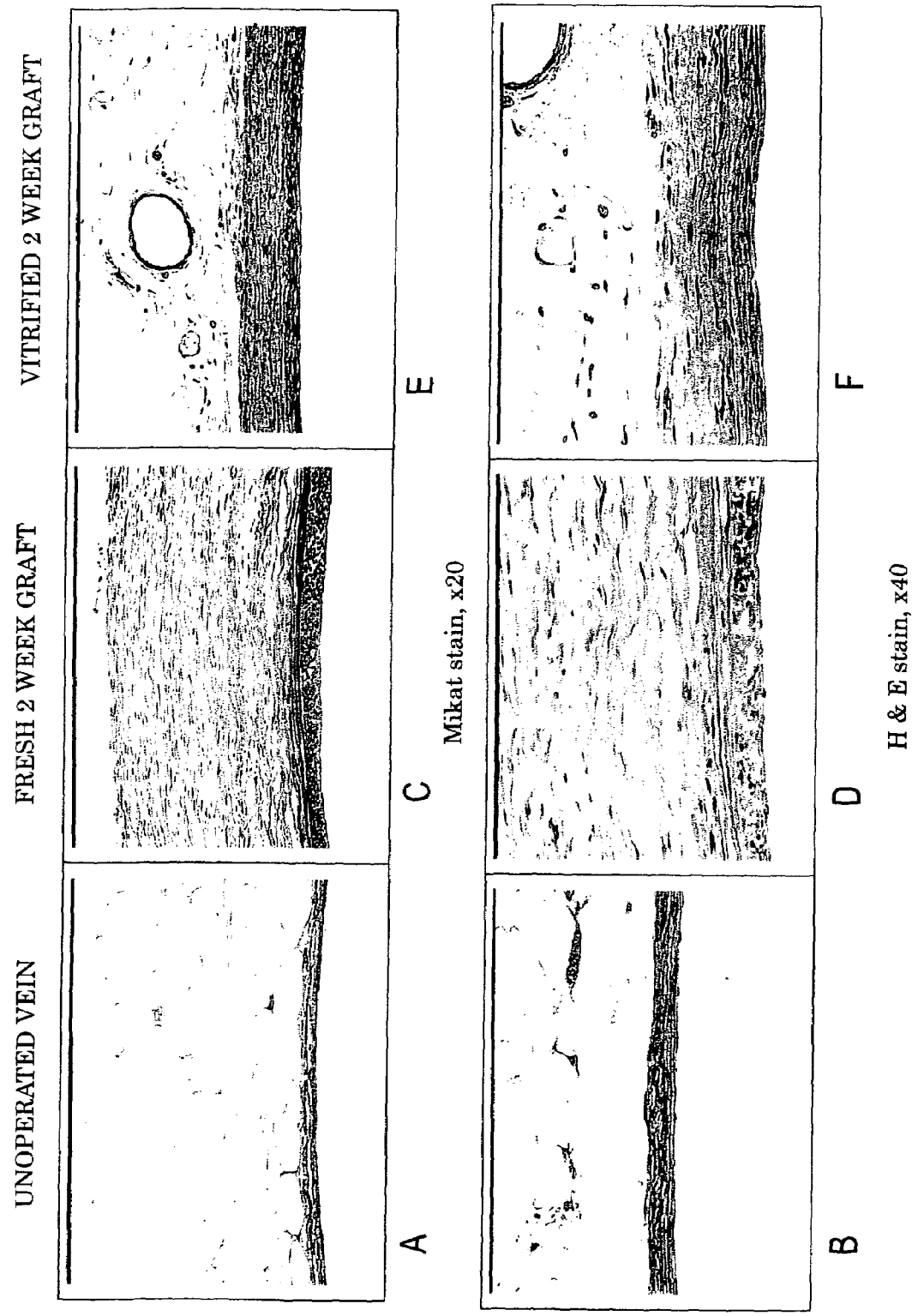
FIGS. 7A–F show the morphology of non-operated veins, fresh vein grafts and vitrified vein grafts in Mikat or H&E staining.

FIG. 7 shows the morphology of non-operated veins, fresh vein grafts and vitrified vein grafts in Mikat or H&E staining. Non-operated control veins showed unaltered endothelial cells on the intimal surface and their walls were composed of a couple of layers of smooth muscle cells (FIG. 7, A-B). At 2 weeks post-transplant, a smooth muscle cell proliferative lesion-intimal hyperplasia and a thickened media appeared in fresh vein grafts (FIG. 7, C-D). Similarly, the vitrified veins developed an intimal hyperplasia layer, which is however, much thinner than fresh vein grafts (FIG. 7, E-F). This study demonstrated that intimal hyperplasia has been reduced in vein grafts pretreated by vitrification. This reduced intimal hyperplasia was a particularly unexpected discovery.

Physiology Study

Vein rings, which are about 4 mm long segments of rabbit external jugular veins, are vitrified in VS55 by the method described above for longer external jugular vein segments, except that perfusion is not used. After being rewarmed, the vein rings are mounted between two stainless steel wire hooks and suspended in a vascular smooth muscle bath containing 5 ml of Krebs Henseleit (KH) solution, which is gassed continuously with 95% $O_2$ and 5% $CO_2$ at 37° C. The baseline tension of all vein rings is adjusted to 0.25 to 0.75 g. Changes in tension are recorded by force transducers. After 1 hour of equilibration, the vein rings are pretested with potassium chloride for contraction. After rinsing with KH solution, the vein rings are equilibrated for another 30 minutes prior to the start of experiment. During a relaxation experiment, contraction of the vein rings is produced by $10^{-6}$M norepinephrine and, after the contractile response plateaus, cumulative concentrations of acetylcholine ($10^{-10}$M to $10^{-4}$M) are added to the bathing medium to induce the endothelium dependent relaxation response.

In the current study, histamine, bradykinin, angiotensin II, and norepinephrine are tested in rabbit jugular vein ring segments vitrified with VS55 and fresh vein rings. Both histamine and bradykinin produce contraction in the vein via their local receptors. Norepinephrine acts directly on the adrenoceptor, while angiotensin II binds to AT receptors and acts through local renin-angiotensin systems.

Table 4 below demonstrates that the vitrified vein rings produce similar contractile function as compared to fresh vein rings.

TABLE 4

Maximal Physiological Responses*

| | Control (g) | Vitrified (g) | % |
|---|---|---|---|
| Histamine | 1.78 ± 0.19 | 1.55 ± 0.27 | 87.1 |
| Bradykinin | 1.75 ± 0.18 | 1.49 ± 0.15 | 85.1 |
| Angiotensin II | 0.58 ± 0.06 | 0.49 ± 0.09 | 84.5 |
| Norepinephrine | 0.99 ± 0.12 | 0.83 ± 0.14 | 83.8 |

*Values expressed as the Mean (± the standard error of the mean (SEM)).
Vitrified vein rings vitrified with vitrification solution VS55 (n = 26).
Control = fresh vein rings (n = 15).
% = percent of corresponding fresh controls.

Artery rings are vitrified in VS55 by the method described above for vein rings. After being rewarmed, norepinephrine and phenylephrine are tested in artery ring segments vitrified with VS55 and fresh artery rings.

Table 5 below demonstrates that the vitrified artery rings produce similar contractile function as compared to fresh artery rings.

TABLE 5

Maximal Physiological Responses*

| | Control (g) | Vitrified (g) | % |
|---|---|---|---|
| Norepinephrine | 2.84 ± 0.38 | 2.58 ± 0.23 | 90.8 |
| Phenylephrine | 2.53 ± 0.45 | 2.23 ± 0.29 | 88.3 |

*Values expressed as the Mean (±SEM).
Vitrified artery rings vitrified with vitrification solution VS55 (norepinephrine n = 37, phenylephrine n = 23).
Control = fresh vein rings (norepinephrine n = 16, phenylephrine n = 12).
% = percent of corresponding fresh controls.

Example 2

Cartilage

Pig cartilage was used in this study. The sample size was varied from 100–300 mg, and >300 mg. The experiments included fresh control and vitrification groups. The tissue viability was tested using Alamar Blue assay.

Outbred pigs of either sex, weighing 30–60 kg, were selected in this pilot study. The animal was weighed and then anesthesia was induced with 33 mg/kg ketamine and 1.1 mg/kg acepromazine, and isoflurane was delivered in oxygen via a face mask. After intubation, anesthesia was maintained using isoflurane delivered in oxygen. Pig knee cartilage was harvested for subsequent studies.

Prior to subzero cooling, the cartilage tissue samples were exposed to the cryoprotectant mixture by adding the vitrification solution VS55 in six steps, for 15 minutes each, on ice (4° C.). This was accomplished in a glass scintillation vial (Dia.×H, 25 mm×60 mm) containing Euro-Collins solution, with successive steps increasing the concentration of cryoprotectant in the solution, until the cartilage samples were immersed in full strength VS55 at 4° C. The surface of the vitrification solution was covered at 4° C. with 0.7 ml of 2-methylbutane to prevent direct contact with air. Samples were cooled rapidly (31° C./min) to −100° C., followed by slow cooling (2° C./min) to −135° C., and finally stored in a freezer at −135° C. for at least 24 hours. Each vitrified cartilage sample was rewarmed in two stages, slow warming to −100° C. (27° C./min) and rapid warming to approximately −35° C. (169° C./min). After the samples were rewarmed, the VS55 was removed in a stepwise manner (seven steps, 15 minutes each, on ice, starting with full strength VS55 and decreasing the concentration of cryoprotectant in the solution in successive steps) to minimize osmotic shock to the cells.

The Alamar Blue assay was employed as a non-cell specific viability assay. This assay was used to determine cell survival following procurement (fresh) and vitrification treatment. It incorporates a water soluble fluorometric viability indicator based on the detection of metabolic activity, specifically, an oxidation-reduction (REDOX) indicator which both fluoresces and changes color in response to chemical reduction of the growth medium caused by cell metabolism. The REDOX indicator has the additional advantage of being minimally toxic to cells and this allows multiple tests to be performed on the same tissue specimen. Aliquots of medium from tissue samples incubated with Alamar Blue working solution for 3–6 hours prior to being placed in microtiter plate wells were read on a microtiter plate spectrofluorometer at 590 nm. The data was normalized to the weight of tissue samples and expressed in percent as the mean±1 se Alamar Blue fluorescence intensity for 11 or more replicate samples of untreated controls.

Figure 8:
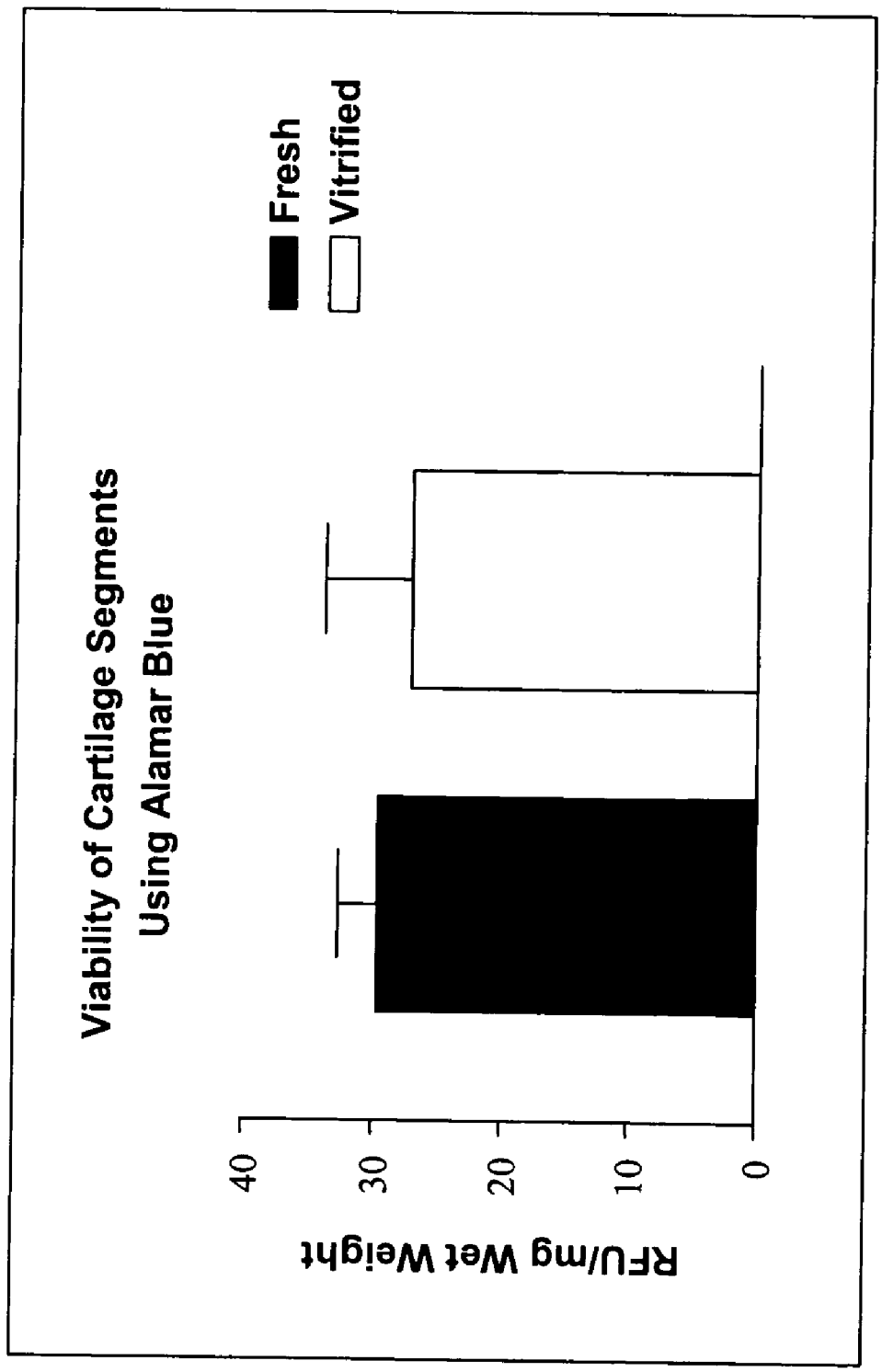
FIG. 8 shows the viability of vitrified cartilage segments.

The results of this pilot study are summarized in FIG. 8. Viability is expressed as relative fluorescence units (RFU) relative to the wet weight of the cartilage (Mean±SEM). Fluorescence was read using the Fmax microplate reader with an excitation wavelength of 544 nm and an emission wavelength of 590 nm. N=15, fresh controls; n=11, vitrified. It can be seen that the average cell survival of vitrified cartilage tissue was about 91.5% (27.13±6.64) compared with fresh controls (29.65±3.04). This study demonstrated that the improved cell recovery in the vitrified cartilage shows that this approach to cryopreservation offers an encouraging solution to the long-term storage of cartilage tissues.

This example, using a novel vitrification approach, showed that a dramatically improved cell survival was achieved by employing vitreous cryopreservation of cartilage. In marked contrast, it has been reported by other investigators that conventional cryopreservation of cartilage reduced the number of viable cells released from the tissue by collagenase/trypsin digestion to less than 20% of fresh control tissue (range 0–20%). These results clearly demonstrate that vitrified cartilage is markedly superior to conventionally cryopreserved cartilage. This example suggests the higher cell recovery in intact articular cartilage is a direct result of avoidance of ice formation, and corroborates the known mechanisms of cryoinjury in multicellular tissues.

Example 3

Additional Tissues

Pigs were selected as an animal model for a source of various tissues for testing the feasibility of vitrification for long-term storage of tissues. The sample size was varied from <100 mg and 100–300 mg. These pilot experiments included fresh control and vitrification groups. The tissue viability was tested using the Alamar Blue assay.

Outbred pigs of either sex, weighing 30–60 kg, were selected in this experiment. The animal was weighed and then anesthesia was induced with 33 mg/kg ketamine and 1.1 mg/kg acepromazine, and isoflurane was delivered in oxygen via a face mask. After intubation, anesthesia was maintained using isoflurane delivered in oxygen. Pig heart valves, myocardium, skin and corneas were harvested for subsequent studies.

Prior to subzero cooling, the tissue samples were exposed to the cryoprotectant mixture by adding the vitrification solution VS55 in six steps, for 15 minutes each, on ice (4° C.). This was accomplished in a glass scintillation vial (Dia.×H, 25 mm×60 mm) containing Euro-Collins solution, with successive steps increasing the concentration of cryoprotectant in the solution, until the samples were immersed in the full strength VS55 at 4° C. The surface of the vitrification solution was covered at 4° C. with 0.7 ml of 2-methylbutane to prevent direct contact with air. Samples were cooled rapidly (20° C./min) to −100° C., followed by slow cooling (2° C./min) to −135° C., and finally stored in a freezer at −135° C. for at least 24 hours. Each vitrified sample was rewarmed in two stages, slow warming to −100° C. (26° C./min) and rapid warming to approximately −35° C. (216° C./min). After the samples were rewarmed, the VS55 was removed in a stepwise manner (seven steps, 15 minutes each, on ice, starting with full strength VS55 and decreasing the concentration of cryoprotectant in the solution in successive steps) to minimize osmotic shock to the cells.

The Alamar Blue assay was employed as a non-cell specific viability assay. This assay was used to determine cell survival following procurement (fresh) and vitrification treatment. Aliquots of medium from tissue samples incubated with Alamar Blue working solution for 2 to 24 hours prior to being placed in microtiter plate wells were read on a microtiter plate spectrofluorometer at 590 nm. The data was normalized to the weight of tissue samples and expressed in percent as the mean±1 se Alamar Blue fluorescence intensity for 6 or more replicate samples of untreated controls.

The results of this study are summarized in Table 6. Viability is expressed as relative fluorescence units (RFU) relative to the wet weight of the tissues (Mean±SEM). Fluorescence was read using the Fmax microplate reader with an excitation wavelength of 544 nm and an emission wavelength of 590 nm. It can be seen that the average viability of vitrified tissues was about 73% (range from 61% to 88%) compared with fresh controls. These examples demonstrate that the improved cell recovery in the vitrified tissues shows this approach to cryopreservation offers an encouraging solution to the long-term storage of tissues.

TABLE 6

|  | Fresh | | Vitrified | | |
| --- | --- | --- | --- | --- | --- |
| Tissues | n | Mean ± SEM (RFU/mg) | n | Mean ± SEM (RFU/mg) | % Fresh |
| Heart Valve | 6 | 56 ± 7 | 10 | 44 ± 15 | 79 |
| Myocardium Tissue | 6 | 24 ± 7 | 12 | 21 ± 3 | 88 |
| Cornea | 6 | 13 ± 5 | 6 | 8 ± 1 | 62 |
| Skin | 6 | 18 ± 8 | 12 | 11 ± 7 | 61 |

SEM is standard error of the mean
n = number of samples tested
% Fresh = average viability of vitrified samples expressed as percentage of fresh controls
RFU = Relative Fluorescence Units

What is claimed is:

1. A method for removing a tissue or organ from vitrification in a solution containing cryoprotectant, comprising:

warming the vitrified tissue or organ in said solution containing cryoprotectant at a rate less than 50° C. per minute to a temperature between −80° C. and the glass transition temperature;

further warming the tissue or organ in said solution at a rate greater than 80° C. per minute to a temperature above −75° C., wherein, at said temperature, the solution is sufficiently fluid that the tissue or organ can be removed therefrom; and immersing the tissue or organ in a series of solutions having decreasing concentrations of cryoprotectant to obtain the tissue or organ in a cryoprotectant-free solution, wherein the method occurs under normal physiological pressure.

2. The method of claim 1, wherein the vitrified tissue or organ is warmed to a temperature between −80° C. and the glass transition temperature at an average rate of from 20 to 40° C. per minute.

3. The method of claim 1, wherein the tissue or organ is warmed from a temperature between −80° C. and the glass transition temperature to a temperature above −75° C. at an average rate of from 200 to 300° C. per minute.

4. The method of claim 3, wherein the tissue or organ is warmed at an average rate of from 200 to 300° C. per minute to a temperature above −35° C.

5. The method of claim 1, wherein each solution of said series of solutions has a temperature above −15° C.

6. The method of claim 1, wherein, in each immersion step, said tissue or organ is also perfused with said solution.

7. The method of claim 1, wherein the tissue or organ is immersed in each solution of said series of solutions for a sufficient time to achieve approximate osmotic equilibration.

8. The method of claim 1, wherein the tissue or organ is immersed in each solution of said series of solutions for at least 10 minutes.

9. The method of claim 1, wherein the tissue or organ is immersed in a series of six solutions having decreasing concentrations of cryoprotectant, wherein the sixth solution is cryoprotectant-free.

10. The method of claim 9, wherein the tissue or organ is immersed in each solution of said series of six solutions for sufficient time to achieve approximate osmotic equilibration.

11. The method of claim 9, wherein the tissue or organ is immersed in each solution of said series of six solutions for at least 10 minutes.

12. The method of claim 9, wherein the cryoprotectant concentration of said six solutions are: 40 to 60% of said concentration sufficient for vitrification; 30 to 45% of said concentration sufficient for vitrification; 15 to 35% of said concentration sufficient for vitrification; 5 to 20% of said concentration sufficient for vitrification; 2.5 to 10% of said concentration sufficient for vitrification; and 0% of said concentration sufficient for vitrification.

13. The method of claim 9, wherein each of said six solutions comprises an osmotic buffering agent.

14. The method of claim 13, wherein said osmotic buffering agent is a low molecular weight osmotic buffering agent.

15. The method of claim 14, wherein said osmotic buffering agent is mannitol.

16. The method of claim 13, further comprising immersing said tissue or organ in a second cryoprotectant-free vehicle solution, which does not contain an osmotic buffering agent, after said immersion in said cryoprotectant-free solution, which does comprise said osmotic buffering agent.

17. The method of claim 1, wherein said tissue or organ is at least one tissue or organ, natural or engineered, vascularized or avascular, selected from the group consisting of blood vessels, musculoskeletal tissue, cartilage, menisci, muscles, ligaments, tendons, skin, cardiovascular tissue, heart valves, myocardium, periodontal tissue, glandular tissue, islets of Langerhans, cornea, ureter, urethra, pancreas, bladder, kidney, breast, liver, intestine and heart.

18. The method of claim 1, wherein said tissue or organ is a blood vessel.

19. The method of claim 1, wherein said tissue or organ is heart valve tissue.

20. The method of claim 1, wherein said tissue or organ is cartilage.

21. The method of claim 1, wherein at least 50% of a measured function of the tissue or organ is maintained as compared to fresh tissues or organs.

22. The method of claim 1, wherein said method is accomplished without perfusing said tissue or organ.

23. A method for vitrification of a tissue or organ and subsequent removal from vitrification, comprising:

immersing the tissue or organ in a series of solutions having increasing concentrations of cryoprotectant to achieve a cryoprotectant concentration sufficient for vitrification, each solution of said series of solutions having a temperature above −15° C.;

cooling the tissue or organ in a solution having said cryoprotectant concentration sufficient for vitrification at an average rate of from 2.5 to 100° C. per minute from a temperature above −15° C. to a temperature between −80° C. and the glass transition temperature;

further cooling the tissue or organ at an average rate less than 30° C. per minute from a temperature that is between −80° C. and the glass transition temperature to a temperature below the glass transition temperature to vitrify the tissue or organ; and removing the tissue or organ from vitrification by the method of claim 1.

24. The method of claim 23, wherein at least 50% of a measured function of the tissue or organ is maintained as compared to fresh tissues or organs.

25. The method of claim 23, further comprising storing the vitrified tissue or organ after cooling and prior to warming.

* * * * *